United States Patent [19]

Jewusiak

[11] Patent Number: 4,638,804
[45] Date of Patent: Jan. 27, 1987

[54] DOUBLE-LATCHED NON-METALLIC, BIO-COMPATIBLE HEMOSTATIC CLIP

[75] Inventor: Stephen J. Jewusiak, Denville, N.J.

[73] Assignee: Ethicon, Inc., Somerville, N.J.

[21] Appl. No.: 744,832

[22] Filed: Jun. 14, 1985

Related U.S. Application Data

[63] Continuation-in-part of Ser. No. 277,582, Jun. 26, 1981, abandoned, which is a continuation-in-part of Ser. No. 123,878, Feb. 25, 1980, abandoned.

[51] Int. Cl.$^4$ ............................................. A61B 17/12
[52] U.S. Cl. ...................................... 128/325; 128/346
[58] Field of Search ............... 128/325, 346, 321, 322, 128/326; 251/9, 10

[56] References Cited

U.S. PATENT DOCUMENTS

| | | | |
|---|---|---|---|
| 3,106,919 | 10/1963 | Churchville | 128/346 |
| 3,171,184 | 3/1965 | Posse | 128/346 X |
| 3,270,745 | 9/1966 | Wood | 128/325 |
| 3,612,475 | 10/1971 | Dinger | 251/10 |
| 3,706,312 | 12/1972 | Melges | 128/346 X |
| 3,713,622 | 1/1973 | Dinger | 251/10 |
| 3,926,195 | 12/1975 | Bieier | 128/346 |
| 4,193,174 | 3/1980 | Stephens | 128/346 X |
| 4,227,730 | 10/1980 | Alexander et al. | 128/346 X |
| 4,386,752 | 6/1983 | Pavlak et al. | 248/73 |
| 4,434,795 | 3/1984 | Mericle | 128/303 R |

FOREIGN PATENT DOCUMENTS

| | | | |
|---|---|---|---|
| 2553540 | 6/1977 | Fed. Rep. of Germany | 128/326 |
| 2732326 | 1/1979 | Fed. Rep. of Germany | 128/346 |
| 972731 | 10/1964 | United Kingdom | 24/16 PB |

OTHER PUBLICATIONS

Secuclip Article.

Primary Examiner—Michael H. Thaler
Attorney, Agent, or Firm—Robert L. Minier

[57] ABSTRACT

Hemostatic clips of absorbable or nonabsorbable polymeric materials are formed by two hinged leg members which interlock at both ends when the clip is closed. The clip is applied to blood vessels or the like with a conventional, forceps-type instrument.

6 Claims, 8 Drawing Figures

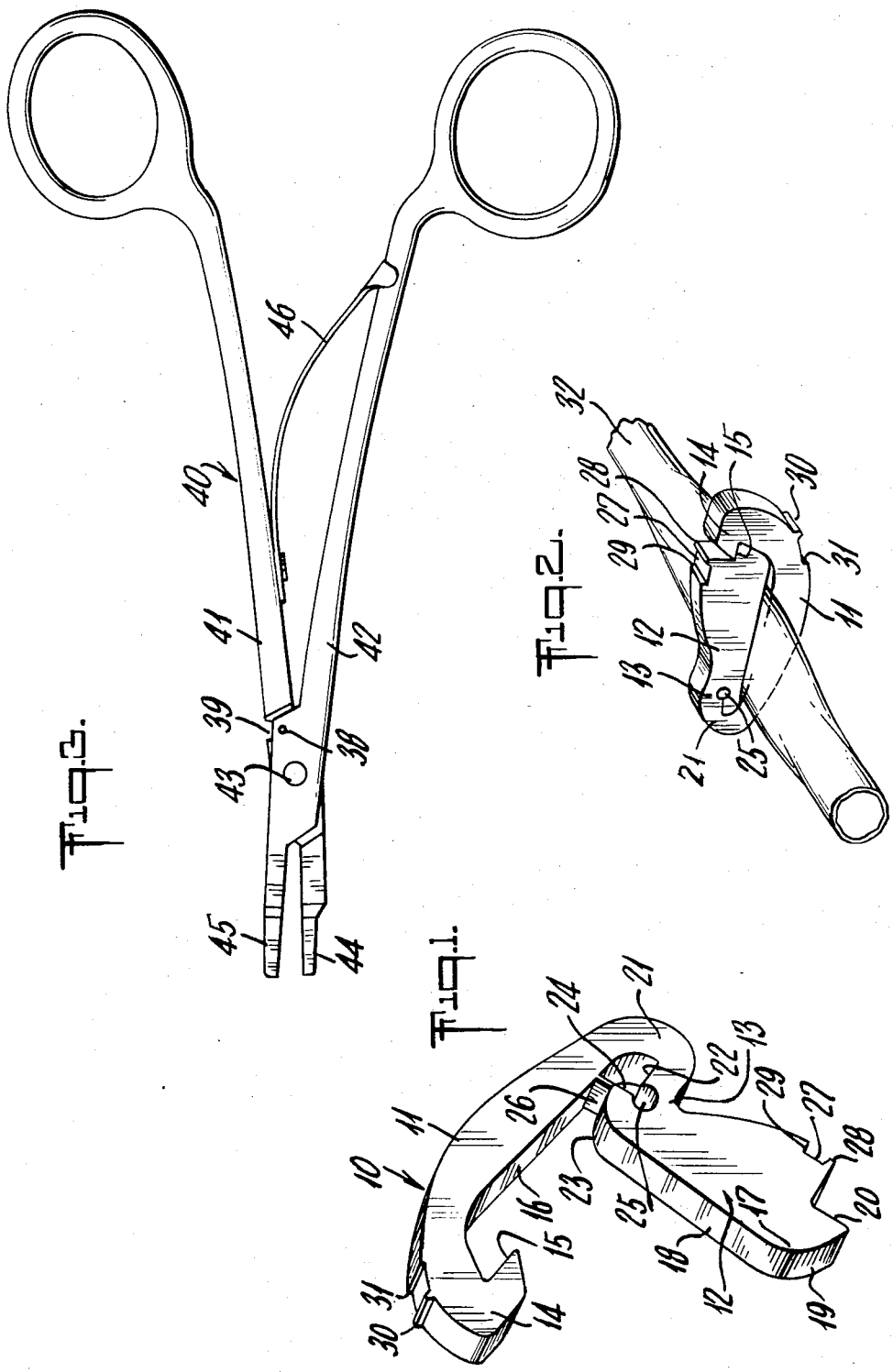

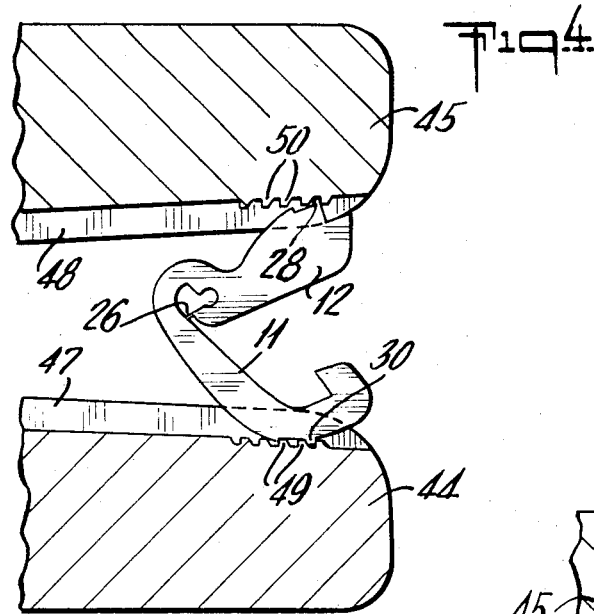
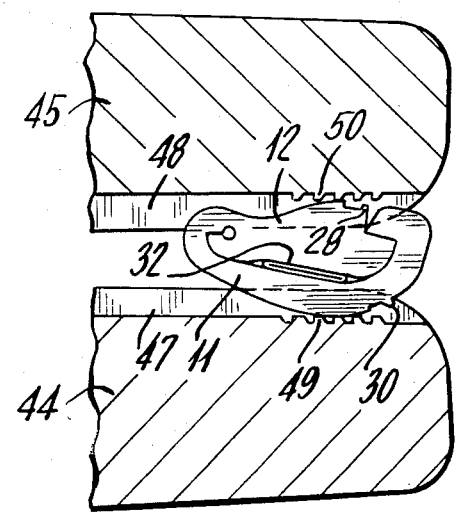
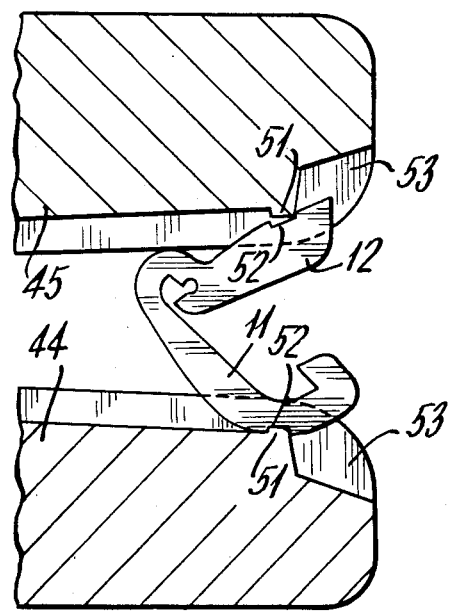

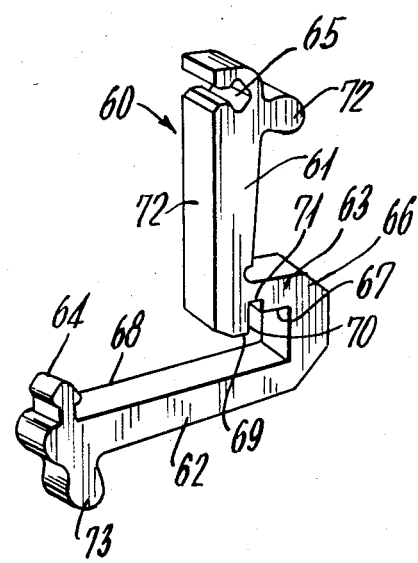
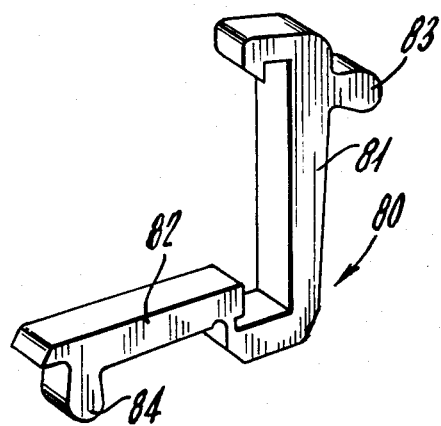

DOUBLE-LATCHED NON-METALLIC, BIO-COMPATIBLE HEMOSTATIC CLIP

The present invention is a continuation-in-part application of my co-pending patent application Ser. No. 277,582 filed June 26, 1981, now abandoned, which is a continuation-in-part patent application of my co-pending application Ser. No. 123,878 filed Feb. 25, 1980, now abandoned.

The present invention relates to hemostatic clips and clip appliers, and, more particularly, to hemostatic clips fabricated from absorbable or nonabsorbable polymeric materials and to instruments for applying such clips to blood vessels and the like.

BACKGROUND OF THE INVENTION

In many surgical procedures, it is often necessary to ligate a plurality of vessels within the surgical site. The vessels may then be severed downstream of the ligated portion. In some instances, the vessel may be ligated at two areas, spaced from one another, and the portion of the vessel between the ligations removed. The primary reason for ligating the vessels is to maintain the surgical site free of an excess of blood and to reduce blood loss in the patient. Also in certain surgical procedures wherein tumors or parts of organs and the like are to be removed, the tumor or organ may have to be separated from certain vessels which before separation, will have to be ligated.

Once a blood vessel is completely shut off, hemostasis; that is, the natural closing of the ligated end of the vessel so as to stop blood flow, will occur in about 3 to 5 days. The body, in the meantime, will continue to allow blood to flow around the ligated area through appropriate capillaries and secondary vessels. The natural physiological functions of the body eventually enlarge these by-pass vessels until adequate blood flow is attained. Hence, when ligating the vessel, there should be a positive stopping of the blood flow in the main vessel; i.e., no leakage, which might cause blood loss in the patient and may disrupt the natural hemostasis and concurrent manufacture of new paths of blood flow in the patient.

In the past, this closing of the vessel was usually accomplished using ligatures; i.e., threads or filaments which the surgeon tied around the vessel desired to be closed. This is a very time-consuming process and one in which positive closure of the vessel was not always accomplished.

In relatively recent years, hemostatic clips have replaced the ligatures in many surgical procedures to close blood vessels and other small fluid ducts. These hemostatic clips have been narrow U-shaped or V-shaped strips formed of tantalum or stainless steel which are capable of being deformed and possess sufficient strength to retain the deformation when clamped about a blood vessel. The clips are generally applied using a forceps-type device having jaws channeled or otherwise adapted to hold the open clip. Representative hemostatic clips and appliers of the prior art are best illustrated in U.S. Pat. Nos. 3,867,944; 3,631,707; 3,439,523; 3,439,522; 3,363,628; 3,312,216; and 3,270,745.

Although the metal hemostatic clips are relatively easy to apply and accomplish a positive closing of the vessel, the metal devices are expensive to manufacture and perhaps more importantly disrupt post operative X-ray procedures and future diagnostic imaging procedures. Hence, it is desired that hemostatic clips be made from materials which will not disrupt the post-operative or other future diagnostic procedures, such as X-ray imaging, computerized axial tomography imaging, and the like.

It is critical that hemostatic clips used in surgery be sterilizable by the well known sterilizing techniques; such as, ethylene oxide treatment, cobalt irradiation, and the like without loss in functionality of the clip.

It has been suggested in the prior art, as in U.S. Pat. No. 3,439,523, for example, that hemostatic clips might be formed of inexpensive plastics or materials which are slowly absorbable in the body. Unfortunately, conventional U and V-shaped hemostatic clips do not possess the required strength or deformability when constructed of known plastic materials to be successfully clamped about a blood vessel. Thus, although the need and desirability of providing inexpensive, non-metallic, bio-compatible ligating clips of both absorbable and non-absorbable materials has been recognized for over ten years, there has been no practical way to satisfy this need.

To accomplish the positive closing of the vessel with non-metallic, bio-compatible hemostatic clips, the vessel clamping surfaces of the clips should have substantially no gap between the surfaces when the clip is closed. Also, the surfaces should be sufficiently smooth and have large enough areas so as not to sever or even partially sever the closed vessel. The non-metallic hemostatic clip, once placed in a clamping position on a vessel, must maintain that position for the period of time required for hemostasis to take place. The clip must maintain its strength in vivo to withstand the pressure trying to force the vessel back open for a sufficient period of time to allow for the natural permanent shutting of the vessel.

The configuration of a hemostatic clip is also important. Because the clip is often used in and around the important organs of the body and the clip is left in the body after the surgical procedure is completed, it is important that the clip be configured to keep trauma within the area; i.e., irritation from a foreign object, to a minimum. Smoothness and size of the clip as well as a lack of projections and a minimum of sharp angles all contribute to reducing the trauma which may occur when placing a foreign object such as a hemostatic clip, within a human body.

The clip configuration is also important to insure the proper placement of a clip. When hemostatic clips are used in a surgical procedure, the general practice is for the nurse to pick up the clip in the jaws of a forceps type applying instrument. The nurse passes the instrument with the clip in place to the surgeon. The surgeon places the jaws of the instrument into the surgical site and around the vessel to be ligated. In many instances, the surgeon will be placing the jaws of the instrument into areas where the surgeon has very limited vision. The surgeon then closes the clip over the vessel to be ligated. All of the handling and manipulation of the instrument must be accomplished without dropping the clip and while maintaining the sterility of the clip.

The size of the clip is also important as the smaller the clip, the less foreign material there is being implanted in the patient. Also, the smaller size allows for more clips to be used in a surgical procedure and in certain instances may simplify the procedure or at least reduce possible side effects resulting from the insertion of foreign objects within the human body.

U.S. Pat. No. 3,926,195 describes a small, plastic clip designed for the temporary or permanent closure of the oviduct and vas deferens in humans. These clips preferably have a clamping surface of from 6 to 10 mm in length and 3 to 6 mm in width. The size of such clips are accordingly considerably larger than is desirable for hemostatic clips. Additionally, clips of U.S. Pat. No. 3,926,195 require the use of several complex tools to apply the clips which are acceptable for the purposes described in the reference but would be unacceptable in a surgical procedure requiring the rapid placement of a large number of hemostatic clips to stem the flow of blood from severed vessels.

In commonly assigned co-pending patent applications Ser. Nos. 49,376 and 49,379 filed June 18, 1979, there are disclosed several configurations of hemostatic clips which possess the advantages and characteristics described herein. Although these clips are especially suitable for surgical procedures, the hinge area in the clips described may, in certain instances, break. This may occur either as the clip is closed or after the clip has been applied to a vessel. Breakage occurs at the hinge area because of the higher stresses found in that area. Though this is an extremely rare occurrence, provided the clips are manufactured correctly and not abused when they are being applied, nevertheless, the closing of the clip and the maintenance of the closed clip is not absolute or foolproof.

Furthermore, in many surgical procedures, it may be desirable to use clips made from an absorbable polymer. Clips made from absorbable polymers have the advantage of not disrupting subsequent X-ray imaging, CAT scanning and the like. Such clips have the added advantage of being totally removed or hydrolyzed by the round physiological functions of the body. However, because of the thinness of the hinge area of the clip and the high stresses in that area, the hinge will be hydrolyzed before the rest of the clip. If the hinge area is hydrolyzed too soon and the clip breaks at that area, the clip will not have performed its desired function.

Also in the design of the clips shown in the prior art, if the hinge area is made too strong and not sufficiently resilient, the closing of the clip may leave a gap immediately adjacent the hinge area which may, in certain instances, be sufficient to prevent the complete closing of a vessel.

While the importance of the clip to the surgical procedure has been discussed, it should be pointed out that the configuration of the clip is also important to the manufacture of the clip. The configuration should be such as to take advantage of simple and economic means of manufacture of the clip such as injection molding. The configuration should be such as to reduce the production of seconds or malformed clips during manufacture. Also, the configuration of the clip should be such as to allow for very simple design of the jaws of the applier to reduce cost of the applier while maintaining the required assurance of holding and setting the clip during the surgical procedure.

It is accordingly an object of the present invention to provide a non-metallic, bio-compatible, hemostatic clip effective for clamping off small blood vessels and other fluid ducts in the body. It is a further object of this invention to provide hemostatic clips of both absorbable and non-absorbable materials. It is yet a further object of this invention to provide non-metallic, biocompatible hemostatic clips which are quickly and easily applied to severed blood vessels and other fluid ducts with a single forceps-type instrument used in applying metallic clips.

SUMMARY OF THE PRESENT INVENTION

The hemostatic clips of the present invention have a positive locking mechanism at both ends of the clip when the clip is in a closed position. The clips of the present invention will not open once they have been closed about a vessel even if the critical hinge area is stressed to the point of breaking or otherwise deteriorates.

The clips of the present invention unexpectedly eliminate the possibility of the formation of a gap adjacent the hinge area of the clip. When the clips of the present invention are made from absorbable polymers, they do not open once they have been closed about a vessel even if there is premature hydrolysis of the hinge area.

The hemostatic clips of the present invention comprise two hinged leg members which interlock at both ends when the clip is closed. The first leg has an elongated vessel clamping portion terminating at its proximal end in a return bend. The second leg is configured to conform to the interior of said first leg. The two leg members are connected at one end by an integral molded hinge extending from the end of the first leg member to a point on the second leg member adjoining said end of the first leg member when the clip is in a closed configuration.

The proximal end of the second leg is adapted to rotate into and engage this hook member when the clip is closed.

The distal ends of the leg members carry locking means to lock the two leg members together when the clip is in the closed position. In a preferred embodiment of the clip of the present invention the distal or free end of the first leg makes a sharp return bend to form a deflectable hook member. The distal end of the second leg is adapted to deflect and engage said hook member when the clip is closed by pivoting the two legs about the hinge point.

The clip is provided in an initially open configuration with the axis of the legs at approximately right angles. The open clip is optionally provided with means for maintaining the clip in an open position until the clip is extentionally closed, such as a thin web extending from the proximal end of the second leg to a near point on the interior surface of the first leg, which web is readily sheared when a closing force is applied to the clip.

The open clip is positioned over the vessel to be ligated with the vessel approximately centered in the clamping portion of the first leg. The second leg is thereupon pivoted about the hinge point until the ends of the second leg are engaged by the hook members of the first leg with the vessel securely compressed between the two leg members. A forceps-type ligating clip applier is useful for positioning and closing the clip.

The clip of the present invention is unique in that once closed, the clip is mechanically locked on both ends, and security of the clip does not depend on the integrity of the hinge element which is the weakest part of the clip, especially when the clip is made from an absorbable polymer.

The clips of the present invention are formed of any suitable, biocompatible polymer by extrusion, injection molding, or other conventional fabrication process. The polymer may be an absorbable material such as homopolymers or copolymers of lactide, glycolide, or p-dioxanone, or a nonabsorbable material such as nylon or polypropylene.

With the novel design of the clips of the present invention, the clip may be made from virtually any polymer. The polymer may be selected based on the desired medical benefits, and the physical characteristics of the polymer such as resiliency and the like are no longer critical. This is an extremely important advance which allows a wide variety of clips to be produced based on their desired medical function and not on other physical characteristics.

DESCRIPTION OF DRAWINGS

FIG. 1 is a greatly enlarged view in perspective of a surgical clip according to the present invention.

FIG. 2 illustrates the clip of FIG. 1 clamped about a blood vessel.

FIG. 3 illustrates a forceps-type applier useful with the clips of the present invention.

FIG. 4 illustrates the open clip of FIG. 1 retained in the jaws of a forceps-type clip applier.

FIG. 5 illustrates the clip of FIG. 4 closed and locked over a blood vessel in the jaws of the applier.

FIG. 6 illustrates an open clip of a modified design retained in the jaws of a forceps-type clip applier.

FIG. 7 illustrates another embodiment of a hemostatic clip in accordance with the present invention.

FIG. 8 illustrates yet another embodiment of a hemostatic clip in accordance with the present invention.

DESCRIPTION OF PREFERRED EMBODIMENT

Referring now to FIG. 1, there is illustrated hemostatic clip 10 constructed of two leg members 11 and 12 connected at the proximal ends thereof by hinge section 13. Leg 11 terminates at the distal end thereof in a return bend forming hook member 14 having inner face 15 substantially parallel to inner face (vessel clamping portion) 16 of leg 11. Leg member 12 terminates at the distal end in end face 19 which joins inner face (vessel clamping portion) 18 of leg 12 through radial surface 17. End face 19 extends to outer surface 20 which is substantially parallel to surface 18. The length of surface 20 is substantially equal to the length of surface 15 to provide secure latching of the clip as hereinafter described.

At the proximal or hinged end of the clip, leg 11 terminates in a return bend forming hook member 21 having an inner face 22 substantially parallel to inner face 16. Leg 12 terminates in radial surface 23 extending to outer surface 24 which is substantially parallel to inner surface 18. Surfaces 22 and 24 are of substantially equal lengths and are separated by cylindrical relief bore 25 defining hinge 13.

As illustrated in FIG. 1, clip 10 includes web 26 extending from the proximal end of leg 12 to the nearest point on surface 16 of leg 11 when legs 11 and 12 are at substantially right angles. Web 26 is an optional structure which functions to stabilize the clip in its open configuration until the web is sheared by a closing force deliberately applied to the clip.

The length and width of faces 16 and 18 are substantially equal, and face 15 of hook 14 is spaced from face 16 of leg 11 by a distance corresponding to the thickness of leg 12 between the plane of face 18 and surface 20. When legs 11 and 12 are pivoted about hinge 13 to bring faces 18 and 16 into opposition, hook 14 is deflected by surface 19 of leg 12 until the distal end of leg 12 snaps under hook 14 and is thereby locked in place. Simultaneously, the proximal end of leg 12 rotates about hinge 13 to engage hook 21 of leg 11 with surfaces 22 and 24 in contact. Web 26, if present, is sheared during closure. The proximal end of the clip is thereby mechanically secured by a hook and latch interaction comparable to that securing the distal end of the clip. The end face of hook member 14 is preferably beveled as illustrated in FIG. 1 to facilitate deflection of the hook to allow passage of leg 12 during clip closure.

The configuration of the clip when closed over a tubular vessel as illustrated in FIG. 2 wherein vessel clamping surfaces 16 and 18 of the clip engage and compress vessel 32 to close the lumen thereof. Surfaces 16 and 18 may be smooth as illustrated in FIG. 1, or may be provided with ridges or grooves to increase vessel holding power. Hinge 13 is seen to extend from the end of hook 21 to a point on leg member 12 adjoining the end of hook 21 when the clip is in a closed position.

Referring again to FIG. 1, leg 12 is provided with applier gripping means near the distal end thereof in the form of channel 27 which forms ridges 28 and 29 extending across the width of the clip. Leg 11 is similarly provided with applier gripping means in the form of ridges 30 and 31 near the distal end thereof. The function of these structural features in positioning the clip in the applier and applying the clip to the vessel being ligated is more fully described hereinafter in regard to FIGS. 4 and 5.

FIG. 3 illustrates a forceps-type ligating clip applier 40 comprising two ring handle members 41 and 42 crossing at hinge point 43 and maintained in a normally open position by spring 46. Handle 41 extends beyond hinge 43 forming jaw member 44 while the extension of handle 42 forms jaw member 45. Pin 38 extends from handle 42 into a blind slot 39 in handle 41 and limits the maximum opening of jaws 44 and 45 to that required to accommodate the open clip.

FIG. 4 illustrates the detail of the construction of jaws 44 and 45 of applier 40 and the interaction of the jaws with the clip of FIG. 1. Jaws 44 and 45 are of identical design and are provided respectively with channels 47 and 48 extending rearwardly from the tips of the jaws. The width of each channel is sufficient to accommodate the width of the clip, and each channel is provided with gear-like teeth 49 and 50 across the bottom of the channel over an area extending rearward from the tips of the jaws. The size and spacing of channel teeth 49 and 50 correspond to the size and spacing of the corresponding ridges 28 and 30 on the clip, and when the open clip is held in the applier, the ridges of the clip mesh with the teeth of the applier as illustrated in FIG. 4. Since the jaws of the applier have identical structure, there is no need to orient the applier to the clip when loading or using the applier.

The clip is initially loaded in the applier in the normally open position as illustrated in FIG. 4. After moving the jaws of the applier and the clip into position over the vessel 32 to be ligated, the jaws of the applier are closed the web 26 sheared, and the clip is locked in position over the vessel 32 as illustrated in FIG. 5. As the jaws of the applier are closed, the legs of clip rotate in the channels of the jaws until the distal end of leg 12 is engaged by the hook member at the distal end of leg 11. Once the clip is fully closed and locked onto the vessel as illustrated in FIG. 5, the jaws of the applier are opened and the applier withdrawn from the site to be reloaded with another clip.

Referring now to FIG. 6, there is illustrated another embodiment of a clip and applier in accordance with the present invention wherein legs 11 and 12 are each provided with a channel 52 extending across the width of the clip near the distal end thereof. Jaws 44 and 45 of the applier are provided with corresponding raised bosses 51 adapted to engage channels 52 when the open clip is positioned between the jaws. The channel of jaw 45 is additionally recessed at 53 to accommodate the hook member at the distal end of leg 11 of the clip when the clip is closed between the jaws. As illustrated, the channel of jaw 44 is similarly recessed to eliminate the necessity for orienting the applier to the clip.

Referring to FIG. 7, there is illustrated a hemostatic clip 60 in accordance with the present invention. The clip 60 is constructed of two leg members 61 and 62 connected at their proximal ends by a hinge section 63. One leg 62 has disposed at its distal end a protrusion 64 while the other leg 61 has disposed at its distal end a recessed area 65 for accepting the protrusion. The protrusion and recessed area are configured so as to be interlocking and provide secure latching when the clip is closed.

At the proximal end or hinged end of the clip, one leg 62 terminates in a return bend forming hook member 66 having an inner face 67 substantially parallel to inner face (vessel clamping portion) 68. The leg 61 terminates in surface 69 extending to surface 70. Surfaces 67 and 70 are substantially equal in length and are separated by area 71.

In use, the vessel to be closed is placed between vessel clamping surfaces 68 and 72 and the clip closed by urging legs 61 and 62 toward each other and closing hinge 63 so that surfaces 67 and 70 contact each other and protrusion 64 is locked into the recess 65.

In the embodiment shown in FIG. 7, the legs carry bosses 72 and 73 which are used to cooperate with recesses in the appropriate applier in order to control the placing and closing of the clip.

The embodiment of the clip 80 depicted in FIG. 8 is similar to that depicted in FIG. 1 with few exceptions. The shape and functioning of the legs 81 and 82 are the same as that described in conjunction with the legs 11 and 12 in FIG. 1. The differences are that in the clip 80, bosses 83 and 84 are used to retain the clip in the applier during application instead of the ridges described in conjunction with FIG. 1 and the shearing web depicted in FIG. 1 is removed from the clip 80.

Although the illustrations and description have been limited to certain specific embodiments of the hemostatic clip of the present invention, many variations in clip design will be apparent to those skilled in the art and are contemplated in the scope of the present invention. For example, the gripping means between the applier jaws and the clip, i.e., the teeth and ridges of FIG. 4 or the boss and channels of FIG. 6 may be omitted. The clips may be fabricated with a smooth outer surface and the jaws of the applier may have smooth channels to accept the clip. Additionally, the channels of the applier may be contoured to the outer configuration of the clip in order to orient and secure the clip between the jaws. These and other modifications in the configuration of the clip may be employed without departing from the spirit and scope of the present invention.

The clips of the present invention may be constructed in various sizes according to their intended function. Hemostatic clips are typically less than 6 mm in length, about 1.5 mm in width, and have a vessel clamping surface about 3 mm in length. The dimensions of the clip may be reduced by about 50 percent for certain applications in microsurgery. Larger clips for special hemostatic applications and other functions such as closure of oviducts or vas deferens may have dimensions of about double those of a typical hemostatic clip. The various sizes of clips are preferably matched with individual appliers having jaws tailored to the size of the clip for best performance.

The clips of the present invention are conveniently molded of biologically acceptable non-metallic materials which may be absorbable or nonabsorbable. Preferred absorbable polymers include homopolymers and copolymers of glycolide, lactide, and p-dioxanone. Preferred nonabsorbable polymers include nylon, polyester and polypropylene. All these materials have been demonstrated to be biologically acceptable when used as sutures or other implantable medical devices. The clips may also be cast or machined from solid polymeric materials.

What is claimed is:

1. A non-metallic, bio-compatible polymeric hemostatic clip capable of being applied to a blood vessel to close said vessel using a clip applying instrument, said clip comprising first and second leg members, each leg member having an outer surface and an inner vessel clamping surface, in opposition to a vessel clamping surface of the leg member;

said first leg member terminating at each end in a return bend forming a hook member extending outward from said vessel clamping surface;

said second leg member terminating at each end in a configuration adapted for engagement by said hook members of said first leg member;

integral resilient hinge means joining said first and second leg members proximal to one end of said leg members;

a shearable web extending from the vessel clamping surface of the first leg member to the proximal end of the second leg member when said clip is in the open position, said web being sheared during closure of the clip;

applier gripping means disposed on the outer surface of said first and second leg members;

said first and second leg members being pivotable about said resilient hinge means from an open position to a closed position with the ends of said second leg member being engaged by the corresponding hook members of the first leg members as said leg members are pivoted to a closed position whereby said clip is maintained the resilient hinge means deteriorates.

2. A clip of claim 1 wherein said hinge means comprises an extension from the end of one hook member to a point on the second leg member adjoining said end of said hook member when said clip is in a closed position.

3. A clip of claim 2 wherein said hinge means defines a cylindrical relief bore extending between said first and second leg members at the end of said hook member.

4. A clip of claim 1 composed of a biologically acceptable absorbable polymer.

5. A clip of claim 4 wherein said polymer is selected from the group consisting of homopolymers and copolymers of glycolide, lactide and p-dioxanone.

6. A clip of claim 1 wherein the applier gripping means comprises a cylindrical boss on the outer surface of each leg member, said boss being disposed transverse of said leg member and extending across the entire width of said leg member.

* * * * *